US011484054B2

(12) United States Patent
Hsin

(10) Patent No.: US 11,484,054 B2
(45) Date of Patent: Nov. 1, 2022

(54) EDIBLE COMPOSITION FOR REDUCING THE DIGESTION OR ABSORPTION OF THE HARMFUL/TOXIC SUBSTANCE

(71) Applicant: Shaochi Hsin, Taipei County (TW)

(72) Inventor: Shaochi Hsin, Taipei County (TW)

(*) Notice: Subject to any disclaimer, the term of this patent is extended or adjusted under 35 U.S.C. 154(b) by 0 days.

(21) Appl. No.: 16/306,317

(22) PCT Filed: Jun. 1, 2016

(86) PCT No.: PCT/CN2016/084307
§ 371 (c)(1),
(2) Date: Nov. 30, 2018

(87) PCT Pub. No.: WO2017/206105
PCT Pub. Date: Dec. 7, 2017

(65) Prior Publication Data
US 2019/0142051 A1    May 16, 2019

(51) Int. Cl.
| | | |
|---|---|---|
| A23L 33/24 | (2016.01) |
| A61P 39/02 | (2006.01) |
| A23L 33/00 | (2016.01) |
| A23L 2/00 | (2006.01) |
| A61K 45/06 | (2006.01) |
| A23L 33/21 | (2016.01) |
| A61P 3/04 | (2006.01) |
| A23L 29/25 | (2016.01) |
| A61P 3/08 | (2006.01) |
| A61K 9/06 | (2006.01) |
| A61K 9/14 | (2006.01) |
| A61K 31/702 | (2006.01) |
| A61K 31/717 | (2006.01) |
| A61K 31/734 | (2006.01) |

(52) U.S. Cl.
CPC ............. *A23L 33/24* (2016.08); *A23L 2/00* (2013.01); *A23L 29/25* (2016.08); *A23L 33/21* (2016.08); *A23L 33/30* (2016.08); *A61K 9/06* (2013.01); *A61K 9/14* (2013.01); *A61K 31/702* (2013.01); *A61K 31/717* (2013.01); *A61K 31/734* (2013.01); *A61K 45/06* (2013.01); *A61P 3/04* (2018.01); *A61P 3/08* (2018.01); *A61P 39/02* (2018.01); *A23V 2002/00* (2013.01)

(58) Field of Classification Search
CPC .......... A23L 33/24; A23L 33/21; A23L 33/30; A23L 33/10; A23L 33/25; A23L 2/00; A23L 29/05; A61K 9/06; A61K 9/14; A61K 31/702; A61K 31/717; A61K 31/734; A61K 45/06; A61P 3/04; A61P 3/08; A61P 39/02; A61P 10/20; A61P 10/30; A23V 2002/02; A23V 2200/334
See application file for complete search history.

(56) References Cited

U.S. PATENT DOCUMENTS

| | | | | |
|---|---|---|---|---|
| 2,043,204 A | * | 6/1936 | Spalding ............... A23L 33/21 |
| | | | | 424/498 |
| 4,156,021 A | | 5/1979 | Richardson | |
| 4,565,702 A | * | 1/1986 | Morley ................. A23L 7/115 |
| | | | | 426/93 |
| 5,589,215 A | | 12/1996 | Tang | |
| 5,609,905 A | * | 3/1997 | Marco ................. A23L 29/238 |
| | | | | 426/469 |
| 6,723,342 B1 | | 4/2004 | Augello et al. | |
| 2002/0193344 A1 | * | 12/2002 | Wolf .................... A23L 29/272 |
| | | | | 514/54 |
| 2003/0059458 A1 | * | 3/2003 | Haber .................... A61K 8/73 |
| | | | | 424/439 |
| 2003/0064104 A1 | * | 4/2003 | Stillman ............... A23K 50/48 |
| | | | | 424/490 |
| 2005/0053676 A1 | * | 3/2005 | Schata ................. A61K 31/704 |
| | | | | 424/724 |
| 2007/0098763 A1 | * | 5/2007 | Sinnott ................. A61K 31/715 |
| | | | | 424/439 |
| 2013/0280292 A1 | | 10/2013 | Hsin | |

FOREIGN PATENT DOCUMENTS

| | | |
|---|---|---|
| CL | 38728 | 7/1993 |
| CN | 1786143 A | 6/2006 |
| CN | 1960714 A | 5/2007 |
| CN | 101284081 A | 10/2008 |
| CN | 102641496 A | 8/2012 |
| EP | 1929873 A1 | 6/2008 |
| JP | 2011-004702 | 1/2011 |
| JP | 2014-506885 | 3/2014 |
| WO | WO 9014017 | 11/1990 |
| WO | WO 95/26643 | 10/1995 |

(Continued)

OTHER PUBLICATIONS

Ross et al., Dietary fiber constituents of selected fruits and vegetables, Published Sep. 1985, J Am Diet Assoc, vol. 85 No. 9, pp. 1111-1116. (Year: 1985).*

Search Report dated Dec. 13, 2019 issued by Brazilian Patent and Trademark Office for counterpart application No. BR112018074747-5.

Office action and search Report dated Feb. 4, 2020 issued by Japan Patent Office for counterpart application No. 2019-516034.

English Abstract Translation of the Officce action and Search Report dated Feb. 4, 2020 issued by Japan Patent Office for counterpart application No. 2019-516034.

(Continued)

*Primary Examiner* — Ali Soroush
(74) *Attorney, Agent, or Firm* — WPAT, P.C., Intellectual Property Attorneys; Anthony King

(57) ABSTRACT

The invention relates to compositions and methods for adjusting digestive or absorptive rates and ratio of foods or drinks or reducing a digestive solution. Particularly, the invention provides a composition comprising an insoluble dietary fiber and a prebiotic gel and its application in reducing digestive or absorptive rates and ratio of foods or drinks.

4 Claims, No Drawings

(56) References Cited

FOREIGN PATENT DOCUMENTS

| WO | WO 00/74501 | | 12/2000 | |
|----|----|----|----|----|
| WO | WO-0074501 A1 | * | 12/2000 | .............. A23P 10/30 |
| WO | WO 2004056375 A1 | | 7/2004 | |
| WO | WO 2005102292 A1 | | 11/2005 | |

OTHER PUBLICATIONS

Office Action and Search Report dated Dec. 31, 2019 issued by Taiwan Intellectual Property Office for counterpart application No. 105117302.

English translation of the Search Report dated Dec. 31, 2019 issued by Taiwan Intellectual Property Office for counterpart application No. 105117302.

New discovery of the action for reducing the concentration of blood alcohol, Asahi Group Holdings [Jan. 28, online],2016], [retrieved on Jan. 28, 2020],URL,https://www.asahigroup - holdings.com/news/2016/0128.html].

Extended Search Report dated Feb. 17, 2020 issued by European Patent Office for EP application 16903490.7.

Office Action dated Feb. 18, 2020 issued by New Zealand Intellectual Property Office for counterpart application 749388.

Office Action dated Jan. 31, 2020 issued by Rospatent, Russian Federal Service for Intellectual Property for counterpart application 2018146595/10.

English Abstract Translation of Office Action dated Jan. 31, 2020 issued by Rospatent, Russian Federal Service for Intellectual Property for counterpart application 2018146595/10.

Office action and search report dated Sep. 11, 2020 issued by Chilean Patent Office for counterpart Chilean Patent Application No. 3414-2018.

English Abstract Translation of the office action and search report dated Sep. 11, 2020 issued by Chilean Patent Office for counterpart Chilean Patent Application No. 3414-2018.

Office action and search report dated Jan. 21, 2021 issued by Chilean Patent Office for counterpart Chilean Patent Application No. 3414-2018.

English Abstract Translation of the office action and search report dated Jan. 21, 2021 issued by Chilean Patent Office for counterpart Chilean Patent Application No. 3414-2018.

* cited by examiner

EDIBLE COMPOSITION FOR REDUCING THE DIGESTION OR ABSORPTION OF THE HARMFUL/TOXIC SUBSTANCE

FIELD OF THE INVENTION

The invention relates to compositions and methods for adjusting digestive or absorptive rates and ratio of foods or drinks or reducing a digestive solution. Particularly, the invention provides a composition comprising an insoluble dietary fiber and a prebiotic gel and its application in reducing digestive or absorptive rates and ratio of foods or drinks.

BACKGROUND OF THE INVENTION

A number of undesired substances exist in aqueous medium, such as pesticides, alcohol, chemicals, antibiotics, heavy metals, additives and hormones. Attention has been focused on the human impacts of undesired substances that are contained in foods or drinks. Accordingly there is a desire to reduce digestive or absorptive rates and ratio of foods or drinks so that the absorption of undesired substances can also be reduced.

Dietary fibers are complex carbohydrate polymers found in plants, which are not digested by the human digestive system, and the fibers are broadly divided into water-soluble and water-insoluble groups. Dietary fibers are resistant to digestion and absorption in the human small intestine, with complete or partial fermentation in the large intestine. Dietary fiber includes polysaccharides, oligosaccharides, lignin, and associated plant substances. Dietary fibers promote beneficial physiologic effects including laxation, and/or blood cholesterol attenuation, and/or blood glucose attenuation. Dietary fibers can change the nature of the contents of the gastrointestinal tract, and to change how other nutrients and chemicals are absorbed through bulking and viscosity. CN1806700A provides a natural purifying agent comprising edible beans, wheat, vegetable, fruits, dry fruit, flavoring, seaweed, starch, chitosan, oligosaccharide, minerals, cellulose, tea, wild plants and cyclodextrin, which can be used to remove harmful substance from food or human body. WO 2012109991 A1 provides a high-molecular-weight fiber and a composition including same; said fiber and said composition can absorb a harmful substance that has entered an organism and eliminate said substance therefrom, preventing the organism from being harmed by said substance. Both did not said about fibers that could reduce digestive or absorptive rates and ratio of foods or drinks.

However, there still is a need to develop a method and composition to reduce digestive or absorptive rate and ratio so that the absorption of undesired substances contained therein can be reduced.

SUMMARY OF THE INVENTION

The invention relates to compositions and its applications in reducing a digestive or absorptive rate and ratio of a food or drink or reducing a digestive solution.

The invention provides a use of a non-digestive immobilized agent or an edible solidifying agent in the manufacture of a preparation for reducing a digestive or absorptive rate and ratio of a food or drink so that substances contained therein are adsorbed by or encapsulated in the immobilized agent or the solidifying agent. In one embodiment, the method and the use can prevent a subject from getting drunk by absorbing alcohol in the drink when the drink is alcoholic, such as wine or alcoholic beverage. In another embodiment, the method and use can reduce weight of a subject by administering the composition of the invention to the subject. Alternatively, the invention provides use of the immobilized agent or solidifying agent in the manufacture of a preparation for reducing weight of a subject.

The invention also provides a use of a non-digestive immobilized agent or an edible solidifying agent in the manufacture of a preparation for absorbing a digestive solution.

In some embodiments, the non-digestive immobilized agent or a solidifying agent is selected from the group consisting of (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonate, alumina, active carbon, silica gel, TiO2, polysaccharide, gluten pellet, fiber or combinations thereof. In one embodiment, the polysaccharide is polysaccharide hydrogel, polysaccharose, glucan, alginate, carrageenan, agar, pectic acid, chitosan, chitin, cellulose, nitrocellulose, hemicellulose, lignin, dietary fiber, gel, cyclodextrin or carboxymethyl cellulose and a combination thereof.

In some embodiments, the edible solidifying agent include, but are not limited to, hydrocolloids, polypeptides, lipids or synthetic and composite edible polymers.

The invention provides an edible composition comprising an insoluble dietary fiber and a prebiotic and liquid-absorbable gel wherein the insoluble dietary fiber is encapsulated in the prebiotic gel. In some embodiments, the insoluble dietary fiber in the edible composition is in a weight ratio ranging from about 15% to about 85% and the prebiotic gel in the edible composition is in a weight ratio ranging from about 15% to about 85%.

In some embodiments, the insoluble dietary fiber useful in the present invention includes, but is not limited to, cellulose, β-glucan, chitin, hemicellulose, hexosan, pentosan, lignin and xanthan, and a combination thereof; the insoluble dietary fiber may be obtained from whole-wheat flour, wheat bran, nut, bean, cauliflower, green bean, pea, potato, phoenix tree (Sterculia BP) or Rhamnus frangula (Frangula BPC). In some embodiments, the prebiotic and liquid-absorbable gel includes, but is not limited to, acacia gum, alpha glucan, beta glucan, guar gum, alginate, carragean, pectin, locust bean gum, konjac, tragacanth gum, karaya gum, arabinoglactin, xanthan gum, inulin, pecticoligosaccharides, resistant starches, retrograded starch, and a combination thereof.

In some embodiments, the composition of the invention is in the form of microparticle, particle or granule. The composition of the invention can be used as food, medical food or food supplement.

In one embodiment, the composition of the invention can be used to reduce a digestive or absorptive rate of a food or drink so that undesired substances contained therein are adsorbed by or encapsulated by the composition. In some embodiments, the harmful/toxic substance is sugar, alcohol, acid, caffeine, base, heavy metal. In some embodiments, the aqueous medium is body fluid (such as digestive juice), alcoholic beverage, beer, coffee or coke.

The invention also provides use of the composition of the invention in the manufacture of a medicament for reducing a digestive or absorptive rate and ratio of a food or drink.

The invention further provides use of the composition of the invention in the manufacture of a preparation for preventing a subject from getting drunk.

DETAILED DESCRIPTION OF THE INVENTION

The invention provides compositions and methods effective to reduce a digestive or absorptive rate and ratio of a food or drink to reduce or prevent the absorption of undesired substances by an animal body. Also, the invention provides compositions and methods for reducing a digestive solution.

All references to singular characteristics or limitations of the present disclosure shall include the corresponding plural characteristic or limitation, and vice versa, unless otherwise specified or clearly implied to the contrary by the context in which the reference is made.

Numerical ranges as used herein are intended to include every number and subset of numbers within that range, whether specifically disclosed or not. Further, these numerical ranges should be construed as providing support for a claim directed to any number or subset of numbers in that range.

The term "or" as used herein is to be understood as "and/or" unless specified otherwise.

The term "about" as used herein is understood to refer to numbers in a range of numerals. Moreover, all numerical ranges herein should be understood to include all integer, whole or fractions, within the range.

The term "solidification" as used herein refers to a process of absorbing a liquid in a material to form a solid or non-flowable material. The term "solidifying agent" is interchangable with "absorbing agent" and it refers to agent performing the solidification process.

The term "stabilization" as used herein refers to a process of transformation harmful/toxic substance to low harmful/toxic substance or digestible or absorptive food/drink to low-flowable material.

The term "immobilization" as used herein refers to the imprisonment of substances in a distinct support or matrix.

The term "adsorption" as used herein is the adhesion of atoms, ions, or molecules from a gas, liquid, or dissolved solid to a surface. Adsorption can include interactions such as hydrophobic or hydrophilic interactions.

The term "microencapsulation" as used herein refers to a process in which tiny particles or droplets are surrounded by a coating to give small capsules of many useful properties.

The term "macroencapsulation" as used herein refers to the envelopment of a large mass of substances in a substrate or matrix.

The term "prebiotic" as used herein means a non-digestible food ingredient that beneficially affects the host by selectively stimulating the growth and/or activity of one or a limited number of bacteria in the digestive tract that can improve the health of the host.

The term "encapsulation" as used herein refers to the inclusion of one thing within another thing so that the included thing is not apparent.

The terms "total dietary fiber" or "dietary fiber" as used herein are understood to be the sum of the soluble and insoluble dietary fiber determined by AACC Method 32-07 and wherein by weight at least 70% of the fiber source comprises dietary fiber.

The term "soluble fiber" as used herein refers to the edible parts of plants or similar carbohydrates resistant to digestion and absorption in the human small intestine with complete or partial fermentation in the large intestine.

The term "insoluble fiber" as used herein refers to the dietary fiber that does not dissolve in water, is metabolically inert and provides bulking, or it can be prebiotic and metabolically ferment in the large intestine. Bulking fibers absorb water as they move through the digestive system, easing defecation.

The "soluble" and "insoluble" dietary fiber is determined using American Association of Cereal Chemists (AACC) Method 32-07. A "soluble" dietary fiber source refers to a fiber source in which at least 60% of the dietary fiber is soluble dietary fiber as determined by AACC Method 32-07, and an "insoluble" dietary fiber source refers to a fiber source in which at least 60% of the total dietary fiber is insoluble dietary fiber as determined by AACC Method 32-07.

As used herein, "food" is a material consisting of protein, carbohydrate and/or fat, which is used in the body of any organism to sustain growth, repair vital processes, and furnish energy. Foods may also contain supplementary substances such as minerals, vitamins, and condiments.

As used herein, a "medical food" is a food that is prescribed by a doctor or a health care professional.

As used herein, "food supplement" is a product that is intended to supplement the diet that bears or contains one or more of the following dietary ingredients: a vitamin, a mineral, an herb or other botanical, an amino acid, a dietary substance for use by man to supplement the diet by increasing the total daily intake, or a concentrate, metabolite, constituent, extract or combination of these ingredients.

The term "subject" as used herein include animals such as mammals, including, but not limited to, primates (e.g., humans), cows, sheep, goats, horses, dogs, cats, rabbits, rats, mice and the like.

In one aspect, the invention provides a method for reducing a digestive or absorptive rate and ratio of a food or drink in a subject, comprising adding a non-digestive immobilized or an edible solidifying agent to a food or drink so that substances contained therein are adsorbed by or encapsulated in the immobilized agent or edible solidifying agent. Accordingly, the invention provides use of a non-digestive immobilized agent or an edible solidifying agent in the manufacture of a preparation for reducing a digestive or absorptive rate and ratio of a food or drink so that substances contained therein are adsorbed by or encapsulated in the immobilized agent or solidifying agent. In one embodiment, the non-digestive immobilized or solidifying agent is in an amount ranging from about 1 to about 50 grams; preferably, about 1 to about 45 grams, about 1 to about 40 grams, about 1 to about 35 grams, about 1 to about 30 grams, about 1 to about 25 grams, about 1 to about 20 grams, about 1 to about 15 grams, about 1 to about 10 grams, about 5 to about 50 grams, about 5 to about 45 grams, about 5 to about 40 grams, about 5 to about 35 grams, about 5 to about 30 grams, about 5 to about 25 grams, about 5 to about 20 grams, about 5 to about 15 grams, about 5 to about 10 grams, about 10 to about 50 grams, about 10 to about 45 grams, about 10 to about 40 grams, about 10 to about 35 grams, about 10 to about 30 grams, about 10 to about 25 grams, about 10 to about 20 grams, about 10 to about 15 grams, about 15 to about 50 grams, about 15 to about 45 grams, about 15 to about 40 grams, about 15 to about 35 grams, about 15 to about 30 grams, about 15 to about 25 grams, about 15 to about 20 grams, about 20 to about 50 grams, about 20 to about 45 grams, about 20 to about 40 grams, about 20 to about 35 grams, about 20 to about 30 grams, about 20 to about 25 grams, about 25 to about 50 grams, about 25 to about 45 grams, about 25 to about 40 grams, about 25 to about 35 grams, about 25 to about 30 grams, about 30 to about 50 grams, about 30 to about 45 grams, about 30 to about 40 grams, about 35 to about 35 grams, about 35 to about 50 grams, about 35 to about 45 grams or about 35 to about 40 grams. In one embodiment, the method and the use can prevent a subject from getting drunk by absorbing alcohol in the drink when the drink is alcoholic, such as wine or alcoholic beverage. In another embodiment, the method and use can reduce weight of a subject by administering the composition of the invention to the subject. Alternatively, the invention provides use of the immobilized agent or solidifying agent in the manufacture of a preparation for reducing weight of a subject.

In one aspect, the invention provides a method for absorbing a digestive solution, comprising administrating a non-digestive immobilized or an edible solidifying agent to a subject. Accordingly, the invention provides use of a non-digestive immobilized agent or an edible solidifying agent in the manufacture of a preparation for absorbing a digestive solution. By reducing the digestive solution in a subject, the obesity, hyperacidity or gastric ulcer may be prevented or treated. In one embodiment, the digestive solution is gastric juice, pancreatic juice or bile. In another embodiment, the non-digestive immobilized or solidifying agent is in an amount ranging from 1 to 50 grams. The preferred amount is as described in the previous paragraph (i.e., paragraph [0037]).

In one embodiment, the encapsulation is macroencapsulation or microencapsulation.

In one embodiment, the non-digestive immobilized agent is liquid-absorbable.

In some embodiments, the edible solidifying agent include, but are not limited to, hydrocolloids, polypeptides, lipids or synthetic and composite edible polymers. In further some embodiments, the hydrocolloid is starch, alginate, carrageenan, carboxymethylcellulose, gum arabic, chitosan, pectin, xanthan gum, agar, gelatin, hydroxypropyl cellulose (HPC), hydroxypropyl methylcellulose (HPMC), carboxymethylcellulose (CMC), or methylcellulose (MC). In further some embodiments, the polypeptide is gelatin, prolamin protein, gluten or mung bean. In further some embodiments, the lipid is acetylated monoglycerides, natural wax, or a surfactant. In further some embodiments, the synthetic and composite edible polymer is polyvinyl acetate, polymethyl methacrylate (PMMA), P (MAA-g-EG), or block copolymers of poly (ethylene oxide) and poly (propylene oxide).

In some embodiments, examples of the non-digestive immobilized agent include, but are not limited to, (poly) tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonate, alumina, active carbon, silica gel, TiO2, polysaccharide, gluten pellet, fiber or combinations thereof. In one embodiment, the polysaccharide is polysaccharide hydrogel, polysaccharose, glucan, alginate (such as sodium alginate or calcium alginate), carrageenan, agar, pectic acid, chitosan, chitin, cellulose, nitrocellulose, hemicellulose, lignin, dietary fiber, gel, cyclodextrin or carboxymethyl cellulose and a combination thereof. In some embodiments, the dietary fiber includes, but is not limited to, cellulose, β-glucan, chitin, hemicellulose, hexosan, pentosan, lignin and xanthan. Whole-wheat flour, wheat bran, nut, bean, cauliflower, green bean, pea, potato, phoenix tree (Sterculia BP) or Rhamnus frangula (Frangula BPC) is good sources of insoluble dietary fiber. In some embodiments, the gel includes, but is not limited to, acacia gum, alpha glucan, beta glucan, guar gum, alginate, carrageen, pectin, locust bean gum, konjac, tragacanth gum, karaya gum, arabinoglactin, xanthan gum, inulin, pecticoligosaccharides, resistant starches, retrograded starch, and a combination thereof.

The method of the invention can reduce a digestive or absorptive rate and ratio of a food or drink to reduce absorption of undesired substances by an animal body or prevent them from absorption by an animal body. The non-digestive immobilized agent or an edible solidifying agent can adsorb, capture or encapsule undesired substances contained in foods or drinks such as harmful or toxic substances; due to the non-digestive property of the immobilized agent, the undesired substances in the immobilized agent can be excreted and will not harm the animal body. For example, the immobilized agent or an edible solidifying agent may solidify or encapsule the undesired substances as a solid, reduce the digestive or absorptive rate and ratio of foods or drinks and reduce surface area of undesired substances that would contact with gastrointestinal tract. The method and use of the invention can reduce a digestive solution of an animal body by using a non-digestive immobilized agent or an edible solidifying agent.

In a further embodiment, the non-digestive immobilized agent or an edible solidifying agent is dehydrated, dried, freezing-dried or granulated. The dehydrated, dried or granulated immobilized agent has an enhanced ability in adsorbing, capturing, solidifying or encapsuling the undesired substances.

In another aspect, the invention provides an edible composition comprising an insoluble dietary fiber and a prebiotic, liquid-absorbable gel wherein the insoluble dietary fiber is encapsulated in the prebiotic and liquid-absorbable gel. In one embodiment, the composition is dehydrated, dried, freezing-dried or granulated.

In some embodiments, the insoluble dietary fiber in the edible composition is in a weight ratio ranging from about 15% to about 85%; preferably, about 20% to about 85%, about 25% to about 85%, about 30% to about 85%, about 35% to about 85%, about 40% to about 85%, about 45% to about 85%, about 50% to about 85%, about 55% to about 85%, about 60% to about 85%, about 65% to about 85%, about 70% to about 85%, about 75% to about 85%, about 75% to about 85%, about 80% to about 85%, about 45% to about 80%, about 45% to about 75%, about 45% to about 70%, about 45% to about 65%, about 45% to about 60%, about 45% to about 55%, about 45% to about 85%, about 50% to about 80%, about 50% to about 75%, about 50% to about 70%, about 50% to about 65%, about 60% to about 70%, about 65% to about 80%, about 65% to about 75% or about 70% to about 80%.

In some embodiments, insoluble dietary fiber useful in the present invention includes, but is not limited to, cellulose, β-glucan, chitin, hemicellulose, hexosan, pentosan, lignin and xanthan, and a combination thereof. Whole-wheat flour, wheat bran, nut, bean, cauliflower, green bean, pea, potato, phoenix tree (Sterculia BP) or Rhamnus frangula (Frangula BPC) is good sources of insoluble dietary fiber.

In some embodiments, the prebiotic and liquid-absorbable gel in the edible composition is in a weight ratio ranging from about 15% to about 85%; preferably, about 20% to about 85%, about 25% to about 85%, about 30% to about 85%, about 35% to about 85%, about 40% to about 85%, about 45% to about 85%, about 50% to about 85%, about 55% to about 85%, about 60% to about 85%, about 65% to about 85%, about 70% to about 85%, about 75% to about 85%, about 15% to about 50%, about 15% to about 45%, about 15% to about 40%, about 15% to about 35%, about 15% to about 30%, about 15% to about 25%, about 20% to about 50%, about 20% to about 45%, about 20% to about 40%, about 20% to about 35%, about 20% to about 30%, about 25% to about 50%, about 25% to about 45%, about 25% to about 40%, about 25% to about 35%, about 30% to about 50% or about 30% to about 40%.

Prebiotics are non-digestible substances that when consumed provide a beneficial physiological effect on the host by selectively stimulating the favorable growth or activity of a limited number of indigenous bacteria. A prebiotic is generally a saccharide that is non-digestible or essentially non-digestible by a human and acts to encourage the growth of probiotic bacteria in the gut, increase adhesion of probiotic bacteria in the gut, displace pathogens, or provide a fermentable dose of carbohydrate to probiotic bacteria (symbiotic) or selected commensal bacteria and increase the levels of those microbial populations (notably lactobacilli and bifidobacteria) in the gastrointestinal tract. A prebiotic can be a saccharide that is non-digestible by the human host and can act as a non-digestible fiber in the diet. This non-digestibility is because humans lack the enzymes to break down some or all of the prebiotic oligosaccharide as it travels through the digestive tract. When a prebiotic reaches the small intestine and colon, bacteria encoding an enzyme or enzymes capable of digesting the prebiotic can break down the prebiotic into simple sugars that the bacteria can use. For example, bifidobacteria and lactobacilli have been reported to digest prebiotic saccharides.

In some embodiments, the prebiotic and liquid-absorbable gel includes, but is not limited to, acacia gum, alpha glucan, beta glucan, guar gum, alginate, carrageen, pectin, locust bean gum, konjac, tragacanth gum, karaya gum, arabinoglactin, xanthan gum, inulin, pecticoligosaccharides, resistant starches, retrograded starch, and a combination thereof.

The compositions described herein may further comprise a filler material that adds bulk to the composition. These filler materials may include any such material suitably known for or otherwise suitable for use in the composition. The composition of the present disclosure may further comprise other optional ingredients that may modify the physical, chemical, aesthetic or processing characteristics of the compositions. In some embodiments, the nutritional compositions may include a flowing agent, a stabilizer, a preservative, an anti-oxidant, an acid, a buffer, a pharmaceutical active, a sweetener, an intense sweetener, a colorant, a flavor, a flavor enhancer, an anti-caking agent, a lubricant, and so forth, as well as any combination thereof.

Preparation of the composition of the invention can be achieved using methods known in the arts. The insoluble dietary fiber may be present in an aqueous medium, at a level to give the insoluble dietary fiber levels in the resulting compositions at the levels disclosed above. Prebiotic gels are generally added during the early part or late phase of encapsulation. The insoluble dietary fibers are suspended in the prebiotic gels and the gels are formed using techniques known in the art.

For example, the prebiotic and liquid-absorbable gel comprises plural groups that can be ionized to form anionic or cationic groups. The presence of such groups in the gel allows the surface of the gel bead to be cross-linked to produce a membrane, when exposed to polymers containing multiple functionalities having a charge opposite to that of the gel. The insoluble dietary fibers suspended in a gellable prebiotic gel medium may be formed into droplets using any suitable method as is known in the art, including but not limited to extrusion from a needle, use of a spray nozzle, or use of a needle and pulsed electrical electrostatic voltage.

The resulting products may be then spray dried, vacuum dried or freeze dried with or without the presence of other carrier solids.

The products formed using prebiotic and liquid-absorbable gels may be porous particles, microparticles or granules so that the aqueous medium containing harmful/toxic substances can easily enter into the particles or granules to contact the insoluble dietary fibers to be absorbed by the fibers. The products can be ground to form powder.

The composition of the invention can be used as food, medical food or food supplement.

In one embodiment, the composition of the invention can be used to reduce a digestive or absorptive rate and ratio of a food or drink, comprising adding a non-digestive immobilized agent to a food or drink so that substances contained therein are adsorbed by or encapsulated in the immobilized agent. In some embodiments, the harmful/toxic substance is sugar, alcohol, acid, caffeine, base, heavy metal. In some embodiments, the aqueous medium is body fluid (such as digestive juice), alcoholic beverage, beer, coffee or coke.

In another embodiment, the composition of the invention can be used to absorb alcohol to avoid getting drunk. In another embodiment, the composition of the invention can be used to absorb caffeine.

In another aspect, the invention provides a method for reducing a digestive or absorptive rate and ratio of a food or drink, comprising adding a composition of the invention to a food or drink so that substances contained therein are adsorbed by or encapsulated in the immobilized agent. Alternatively, the invention provides use of the composition of the invention in the manufacture of a medicament for reducing a digestive or absorptive rate and ratio of a food or drink.

In a further aspect, the invention provides a method for preventing a subject from getting drunk, comprising administering the composition of the invention to the subject before or after the subject drinks an alcoholic beverage. Alternatively, the invention provides use of the composition of the invention in the manufacture of a preparation for preventing a subject from getting drunk.

In another further aspect, the invention provides a method for reducing weight of a subject, comprising administering the composition of the invention to the subject. Alternatively, the invention provides use of the composition of the invention in the manufacture of a preparation for reducing weight of a subject.

The insoluble dietary fiber has a feature in absorption of an aqueous medium; by utilizing this feature, the undesired substances (such as harmful/toxic substances) contained in foods or drinks can be adsorb and then removed. Therefore, the composition of the invention can be widely applied in various fields.

The examples below are intended to further illustrate certain aspects of the methods and compounds described herein, and are not intended to limit the scope of the claims.

EXAMPLE

Example 1

Composition of the Invention in Reducing Blood Alcohol Concentration

The clinical effects of the composition of the invention (85% karaya gum+15% cellulose; named as SACA) on absorbing alcohol and lowering the serum level of ethanol were tested.

5 g of SACA and 100 mL of sorghum wine (58% alcohol) were administered to experimental group with 3 subjects; and 100 mL of sorghum wine (58% alcohol) was administered to control group with 3 subjects. The alcohol blood concentrations (mg/dl) were determined after drinking. The testing and the results are shown in the table below.

| Sampling Time after drinking | Average alcohol blood concentration (mg/dl) | |
|---|---|---|
| | Control group | Experimental Group |
| 15 minutes | 44 | 30 |
| 30 minutes | 61 | 41 |
| 45 minutes | 98 | 50 |
| 60 minutes | 101 | 51 |

As shown in the above table, the alcohol blood concentrations of the experimental group reduce 32%, 33%, 49% and 50% respectively after drinking 15 mins, 30 mins, 45 mins and 60 mins, compared to the control group.

10 g of SACA and 250 mL of brandy wine (40% alcohol) were administered to experimental group with 3 subjects; and 100 mL of brandy wine (40% alcohol) was administered to control group with 3 subjects. The alcohol blood concentrations (mg/dl) were determined after drinking. The testing and the results are shown in the table below.

| Sampling Time after drinking | Average alcohol blood concentration (mg/dl) | |
|---|---|---|
| | Control group | Experimental Group |
| 5 minutes | 46 | 20 |
| 10 minutes | 47 | 30 |
| 20 minutes | 76 | 27 |
| 30 minutes | 102 | 26 |

As shown in the above table, the alcohol blood concentrations of the experimental group reduce 56%, 36%, 64% and 75% respectively after drinking 5 mins, 10 mins, 20 mins and 30 mins, compared to the control group.

Example 2

Composition of the Invention in Reducing Blood Sugar Concentration

The clinical effects of the composition of the invention (85% karaya gum+15% cellulose; named as SACA) in reducing blood sugar concentrations (mg/dL) were tested.

The fasting subjects of control group drank 100 mL glucose (75 g) solution and the fasting subjects of experimental groups drank 100 mL glucose (75 g) solution and 10 g of SACA. Then, the blood sugar concentrations were measured every 30 minutes. The results are shown in below table.

| | Blood alcohol concentration (mg/dL) | | | |
|---|---|---|---|---|
| | Subject 1 | | Subject 2 | |
| Time | Control group | Experimental group | Control group | Experimental group |
| 0 | 88 | 85 | 70 | 75 |
| 30 | 135 | 127 | 104 | 93 |
| 60 | 131 | 114 | 128 | 90 |
| 90 | 111 | 113 | 121 | 108 |
| 120 | 88 | 97 | 125 | 98 |

As shown in the above table, the blood sugar concentrations of the experimental group significantly reduce compared to the control group.

What is claimed is:

1. A method for reducing a digestive or absorptive rate and ratio of a food or drink in a subject, comprising administering to said subject an effective amount of an edible composition comprising an insoluble dietary fiber and a prebiotic and liquid-absorbable gel, wherein the insoluble dietary fiber is encapsulated in the prebiotic and liquid-absorbable gel, wherein the insoluble dietary fiber in the edible composition is at a weight ratio of about 15% and the prebiotic and liquid-absorbable gel in the edible composition is at a weight ratio of about 85%, wherein the prebiotic and liquid-absorbable gel is porous, wherein the insoluble dietary fiber is cellulose, and wherein the prebiotic and liquid-absorbable gel is karaya gum.

2. The method of claim 1, wherein the method prevents a subject from getting drunk or reducing a weight of a subject.

3. The method of claim 1, wherein the encapsulation is macroencapsulation or microencapsulation.

4. The method of claim 1, wherein the edible composition is further dehydrated, dried, freezing-dryied or granulated.

* * * * *